(12) United States Patent
Ruaud

(10) Patent No.: US 6,452,074 B1
(45) Date of Patent: Sep. 17, 2002

(54) INBRED CORN LINE TDC1

(75) Inventor: Pierre Ruaud, Marcellus (FR)

(73) Assignee: Limagrain Genetics Grande Culture S.A. (FR)

( * ) Notice: Subject to any disclaimer, the term of this patent is extended or adjusted under 35 U.S.C. 154(b) by 0 days.

(21) Appl. No.: 09/725,956

(22) Filed: Nov. 30, 2000

(51) Int. Cl.⁷ .............................. A01H 5/00; A01H 5/10; A01H 1/00; A01H 1/02; C12N 5/04
(52) U.S. Cl. .................... 800/320.1; 800/265; 800/266; 800/267; 800/268; 800/274; 800/275; 800/278; 800/279; 800/300.1; 800/302; 800/303; 435/412; 435/413; 435/418; 435/419; 435/421; 435/424; 435/430; 435/430.1; 435/468
(58) Field of Search .................................. 800/265, 266, 800/267, 268, 274, 275, 278, 279, 300.1, 302, 303, 320.1; 435/412, 413, 418, 419, 421, 424, 430, 430.1, 468

(56) References Cited

U.S. PATENT DOCUMENTS 5,973,238 A  * 10/1999  Miller ..................... 800/320.1

* cited by examiner

*Primary Examiner*—David T. Fox
(74) *Attorney, Agent, or Firm*—Rothwell, Figg, Ernst & Manbeck

(57) ABSTRACT

An inbred corn line, designated TDC1, is disclosed. The invention relates to the seeds of inbred corn line TDC1, to the plants of inbred corn line TDCI and to methods for producing a corn plant produced by crossing the inbred line TDC1 with itself or another corn line. The invention further relates to hybrid corn seeds and plants produced by crossing the inbred line TDC1 with another corn line.

29 Claims, No Drawings

INBRED CORN LINE TDC1

BACKGROUND OF THE INVENTION

The present invention relates to a new and distinctive corn inbred line, designated TDC1. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, resistance to diseases and insects, better stalks and roots, tolerance to drought and heat, reduction of the time to crop maturity and better agronomic quality. With mechanical harvesting of many crop, uniformity of plant characteristics such as germination and stand establishment, growth rate, maturity and plant and ear height is important.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three years at least. The best lines are candidates for new commercial cultivars; those elite in traits are used as parents to produce new populations for further selection.

These processes, which lead to the final step of marketing and distribution, usually take from eight to twelve years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior corn inbred lines and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same corn traits.

Each year, the plant breeder selects the germplasm to advance to the next generation. This germplasm is grown under unique and different geographical, climatic and soil conditions, and further selections are then made, during and at the end of the growing season. The inbred lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop a superior new corn inbred line.

The development of commercial corn hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes. The new inbreds are crossed with other inbred lines and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating).

Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_8$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., Allard, R. W. "Principles of Plant Breeding" John Wiley and Son, pp.115–161, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as the homogeneity of the inbred parent is maintained. A single-cross hybrid is produced when two inbred lines are crossed to produce the F. progeny. A double-cross hybrid is produced from four inbred lines crossed in pairs (A×B and C×D) and then the two $F_1$ hybrids are crossed again (A×B)×(C×D). Much of the hybrid vigor exhibited by $F_1$ hybrids is lost in the next generation. Consequently, seed from hybrid varieties is not used for planting stock.

Hybrid maize seed is typically produced by manual or mechanical detasseling. Alternate strips of two maize inbreds are planted in a field, and the pollen-bearing tassels are removed from one of the inbreds (female). Providing that there is sufficient isolation from sources of foreign maize pollen, the ears of the detasseled inbred will be fertilized only from the other inbred (male), and the resulting seed is therefore hybrid and will form hybrid plants.

The laborious, and occasionally unreliable, detasseling process can be avoided by using cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile.

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511, all patents referred to being incorporated by reference.

Another system useful in controlling male sterility makes use of gametocides. Gametocides are not a genetic system, but rather a topical application of chemicals. These chemicals affect cells that are critical to male fertility. The application of these chemicals affects fertility in the plants only for the growing season in which the gametocide is applied (see Carlson, Glenn R., U.S. Pat. No. 4,936,904). Application of the gametocide, timing of the application and genotype specificity often limit the usefulness of the approach.

Corn is an important and valuable field crop. Thus, a continuing goal of plant breeders is to develop stable, high yielding corn hybrids that are agronomically sound. The reasons for this goal are obviously to maximize the amount of grain produced on the land used and to supply food for both animals and humans. To accomplish this goal, the corn breeder must select and develop corn plants that have the traits that result in superior parental lines for producing hybrids.

SUMMARY OF THE INVENTION

According to the invention, there is provided a novel inbred corn line, designated TDC1. This invention thus relates to the seeds of inbred corn line TDC1, to the plants of inbred corn line TDC1 and to methods for producing a corn plant produced by crossing the inbred line TDC1 with itself or another corn line. This invention further relates to hybrid corn seeds and plants produced by crossing the inbred line TDC1 with another corn line.

The inbred corn plant of the invention may further comprise, or have, a cytoplasmic factor, or other factor, that is capable of conferring male sterility. So, the invention further comprises a male sterile form of the inbred. Parts of the corn plant of the present invention are also provided, such as e.g., pollen obtained from an inbred plant and an ovule of the inbred plant.

In one aspect, the present invention provides regenerable cells for use in tissue culture or inbred corn plant TDC1. The tissue culture will preferably be capable of regenerating plants having the physiological and morphological characteristics of the foregoing inbred corn plant, and of regenerating plants having substantially the same genotype as the foregoing inbred corn plant. Preferably, the regenerable cells in such tissue cultures will be embryos, protoplasts, meristematics cells, callus, pollen, leaves, anthers, roots, root tips, silk, kernels, ears, cobs, husk or stalks. Still further, the present invention provides corn plant regenerated from the tissue cultures of the invention.

Another objective of the invention is to provide methods for producing other inbred corn plants derived from inbred corn line TDC1. Inbred corn lines derived by the use of those methods are also part of the invention.

The invention also relates to methods for producing a corn plant containing in its genetic material one or more transgenes and to the transgenic corn plant produced by that method.

In another aspect, the present invention provides for single gene converted plants of TDC1. The single transferred gene may preferably be a dominant or recessive allele. Preferably, the single transferred gene will confer such trait as male sterility, herbicide resistance, insect resistance, resistance for bacterial, fungal, or viral disease, male fertility, enhanced nutritional quality, and industrial usage. The single gene may be a naturally occurring maize gene or a transgene introduced through genetic engineering techniques.

The invention further provides methods for developing corn plant in a corn plant breeding program using plant breeding technique including recurrent selection, backcrossing, pedigree breeding, restriction fragment length polymorphism enhanced selection, genetic marker enhanced selection and transformation. Seeds, corn plant, and parties thereof produced by such breeding methods are also part of the invention.

DEFINITIONS

In the description and tables which follow, a number of terms are used. In order to provide a clear and consistent understanding of the specification and claims, including the scope to be given such terms, the following definitions are provided:

Allele. The allele is any of one or more alternative form of a gene, all of which alleles relates to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid F. with one of the parental genotype of the $F_1$ hybrid.

Essentially all the physiological and morphological characteristics. A plant having essentially all the physiological and morphological characteristics means a plant having the physiological and morphological characteristics, except for the characteristics derived from the converted gene.

Regeneration. Regeneration refers to the development of a plant from tissue culture.

Single gene converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Predicted RM. This trait for a hybrid, predicted relative maturity (RM), is based on the harvest moisture of the grain. The relative maturity rating is based on a known set of checks and utilizes conventional maturity such as the Comparative Relative Maturity Rating System or its similar, the Minnesota Relative Maturity Rating System.

MN RM. This represents the Minnesota Relative Maturity Rating (MN RM) for the hybrid and is based on the harvest moisture of the grain relative to a standard set of checks of previously determined MN RM rating. Regression analysis is used to compute this rating.

Yield (Bushels/Acre). The yield in bushels/acre is the actual yield of the grain at harvest adjusted to 15.5% moisture.

Moisture. The moisture is the actual percentage moisture of the grain at harvest.

GDU Silk. The GDU silk (=heat unit silk) is the number of growing degree units (GDU) or heat units required for an inbred line or hybrid to reach silk emergence from the time of planting. Growing degree units are calculated by the Barger Method, where the heat units for a 24-hour period are: GDU=((Max Temp+Min Temp)/2)−50 The highest maximum used is 86° F. and the lowest minimum used is 50° F. For each hybrid, it takes a certain number of GDUs to reach various stages of plant development. GDUs are a way of measuring plant maturity.

Stalk Lodging. This is the percentage of plants that stalk lodge, i.e., stalk breakage, as measured by either natural lodging or pushing the stalks determining the percentage of plants that break off below the ear. This is a relative rating of a hybrid to other hybrids for standability.

Root Lodging. The root lodging is the percentage of plants that root lodge; i.e., those that lean from the vertical axis at an approximate 30° angle or greater would be counted as root lodged.

Plant Height. This is a measure of the height of the hybrid from the ground to the tip of the tassel, and is measured in centimeters.

Ear Height. The ear height is a measure from the ground to the ear node attachment, and is measured in centimeters.

Dropped Ears. This is a measure of the number of dropped ears per plot, and represents the percentage of plants that dropped an ear prior to harvest.

Stay Green. Stay green is the measure of plant health near the time of black layer formation (physiological maturity). A high score indicates better late-season plant health.

DETAILED DESCRIPTION OF THE INVENTION

Inbred corn line TDC1 is a yellow flint dent corn with superior characteristics, and provides an excellent parental line in crosses for producing first generation ($F_1$) hybrid corn. Inbred corn line TDC1 is best adapted to the North Corn Belt, Northern regions of the U.S. and Southern Ontario and can be used to produce hybrids having a relative maturity of approximately 85–90 days on the Comparative Relative Maturity Rating System for harvest moisture of grain. Inbred corn line TDC1 shows an excellent seedling vigor, an early pollen shed, excellent brittle stalk resistance, good husk cover, above average stay green, resistance to Head Smut and Northern Corn Leaf Blight, and late plant intactness.

TDC1 is similar to MA75211, a proprietary inbred owned by Limagrain, however there are numerous differences including the fact that TDC1 flowers substantially earlier than MA75211. Hybrids with TDC1 also are less susceptible to stalk breakage.

TDC1 is an inbred line with very high yield potential and average to good stalk and roots in hybrids. TDC1 has a plant height of 172 cm with an average ear insertion of 76 cm. The kernels are arranged in distinct straight rows on the ear. Heat units to 50% pollen shed are approximately 1308 and to 50% silk are approximately 1339.

Some of the criteria used to select ears in various generations include: yield, stalk quality, root quality, disease tolerance, late plant greenness, late season plant intactness, ear retention, ear height, pollen shedding ability, silking ability, and corn borer tolerance. During the development of the line, crosses were made to inbred testers for the purpose of estimating the line's general and specific combining ability, and evaluations were run in France, in Canada by the Chatham Research Station and in the U.S. by the Kirkland, Illinois Research Station. The inbred was evaluated further as a line and in numerous crosses by the Chatham and Kirkland stations and other research stations across the Corn Belt. The inbred has proven to have a good combining ability in hybrid combinations.

The inbred line has shown uniformity and stability for the traits, as described in the following variety description information. It has been self-pollinated a sufficient number of generations with careful attention to uniformity of plant type. The line has been increased with continued observation for uniformity. No variant traits have been observed or are expected in TDC1.

Inbred corn line TDC1 has the following morphologic and other characteristics (based primarily on data collected at Kirkland, Ill. and Champaign, Ill.).

Variety Description Information

1. TYPE: Dent
2. REGION WHERE DEVELOPED: France
3. MATURITY:

|  | Days | Heat Units |
|---|---|---|
| From emergence to 50% of plants in silk: | 58 | 1340 |
| From emergence to 50% of plants in pollen: | 56.5 | 1309 |

Heat Units:=GDU=((Max Temp+Min Temp)/2)−50

4. PLANT:
   Plant Height to tassel tip: 172.05 cm (Standard Deviation=6.02)
   Ear Height to base of top ear: 76.00 cm (6.36)
   Average Length of Top Ear Internode: 9.83 cm (1.66)
   Average number of Tillers: 0 (0)
   Average Number of Ears per Stalk: 1.1 (0.30)
   Anthocyanin of Brace Roots: faint
5. LEAF:
   Width of Ear Node Leaf: 8.61 cm (0.50)
   Length of Ear Node Leaf: 71.48 cm (2.76)
   Number of leaves above top ear: 5.30 (0.47)
   Leaf Angle (from 2nd Leaf above ear at anthesis to Stalk above leaf): 6.21° (3.16)
   Leaf Color: Medium Green Munsell Code 7.5GY 3/4
   Leaf Sheath Pubescence (Rate on scale from 1=none to 9=like peach fuzz): 3.5
   Marginal Waves (Rate on scale from 1=none to 9=many): 7
   Longitudinal Creases (Rate on scale from 1=none to 9=many): 4
6. TASSEL:
   Number of Lateral Branches: 4.15 (1.21)
   Branch Angle from Central Spike: 46.70 (6.63)
   Tassel Length (from top leaf collar to tassel top): 31.68 cm (1.69)
   Pollen Shed (Rate on scale from O=male sterile to 9=heavy shed): 7
   Anther Color: Pale Purple Munsell Code 2.5R 6/6
   Glume Color: Medium Green Munsell Code 5GY 5/10
   Bar Glumes: absent
7a. EAR: (Unhusked Data)
   Silk Color (3 days after emergence): Green yellow Munsell Code 2.5GY 8/8
   Fresh Husk Color (25 days after 50% silking): Medium Green Munsell 5GY 6/6
   Dry Husk Color (65 days after 50% silking): Light Green Munsell Code 2.5GY 8/4
   Position of Ear: upright
   Husk Tightness (Rate on scale from=very loose to 9=very tight): 5.5
   Husk Extension at harvest: medium (<8 cm)
7b. EAR: (Husked Ear Data)
   Ear Length: 13.08 cm (0.69)
   Ear Diameter at mid-point: 37.27 mm (1.11)
   Ear Weight: 78.45 gm (12.96)
   Number of Kernel Rows: 12.5 (1.58)
   Kernel Rows: distinct
   Row Alignment: straight
   Shank Length: 8.11 cm (1.45)
   Ear Taper: average
8. KERNEL: (Dried)
   Kernel Length: 9.45 mm (0.51)
   Kernel Width: 7.95 mm (0.56)
   Kernel Thickness: 5.01 mm (0.76)
   Round Kernels (Shape Grade): 42.28 % (12.55)
   Aleurone Color Pattern: homozygous
   Aleurone Color: colorless
   Hard Endosperm Color: yellow (Munsell code 5Y 8/12)
   Endosperm Type: normal starch
   Weight per 100 kernels (unsized sample): 22.1 gm (1.72)
9. COB:
   Cob Diameter at Mid-Point: 23.83 mm (0.81)
   Cob Color: Pink orange Munsell code 2.5YR 7/6
10. AGRONOMIC TRAITS:
    Stay Green (at 65 days after anthesis) (Rate on scale from 1=worst to 9=excellent): 7
    0% Dropped Ears (at 65 days after anthesis)
    0% Pre-anthesis Brittle Snapping
    0% Pre-anthesis Root Lodging
    0% Post-anthesis Root Lodging (at 65 days after anthesis)
    Yield of Inbred Per Se (at 12–13% grain moisture): 21 Bu/Acre Tables In the tables that follow, the traits and characteristics of inbred corn line TDC1 are given in hybrid combination. The data collected on inbred corn line TDC1 is presented for the key characteristics and traits. The tables present yield test information about TDC1. TDC1 was tested in several hybrid combinations at numerous locations, with two or three replications per location. Information about these hybrids, as compared to several check hybrids, is presented.

The first pedigree listed in the comparison group is the hybrid containing TDC1. Information for the pedigree includes:

1. Mean yield in Qx/Ha of the hybrid across all locations (Mean Yield) is shown in column 2.
2. A mean for the percentage moisture (% Moist) for the hybrid across all locations is shown in column 3.
3. A mean of the yield divided by the percentage moisture (Y/M) for the hybrid across all locations is shown in column 4.
4. A mean of the percentage of plants with stalk lodging (% Stalk) across all locations is shown in column 5.

| | Overall Comparisons Hybrid vs. Check Hybrids Location: France, 1994 | | | |
|---|---|---|---|---|
| Pedigree | Mean Yield | % Moist | Y/M | % Stalk |
| TDC1*SN87165 At 6 Locations | 109.5 | 26.3 | 2 | 6 |

-continued

Overall Comparisons
Hybrid vs. Check Hybrids
Location: France, 1994

| Pedigree | Mean Yield | % Moist | Y/M | % Stalk |
|---|---|---|---|---|
| As Compared to: | | | | |
| Barbara | 103.3 | 26.9 | 7 | 15 |
| Carla | 94.4 | 27.4 | 8 | 14 |
| Furio | 105.6 | 27.8 | 12 | 9 |

TABLE 2

Overall Comparisons
Hybrid vs. Check Hybrids
Location: France, 1995

| Pedigree | Mean Yield | % Moist | Y/M | % Stalk |
|---|---|---|---|---|
| TDC1*SN87165 At 7 Locations As Compared to: | 116.5 | 28.8 | 8 | 12 |
| Barbara | 106.1 | 27.9 | 19 | 20 |
| Carla | 104.3 | 30.6 | 7 | 21 |
| DK300 | 94.2 | 31.9 | 16 | 5 |

TABLE 3

Overall Comparisons
Hybrid vs. Check Hybrids
Location: France, 1996

| Pedigree | Mean Yield | % Moist | Y/M | % Stalk |
|---|---|---|---|---|
| TDC1*SN87165 At 11 Locations As Compared to: | 110.8 | 28.5 | 6 | 12 |
| Barbara | 97.1 | 28 | 15 | 16 |
| Carla | 100.5 | 29.1 | 8 | 33 |
| Cherif | 103.7 | 27.6 | 8 | 0 |
| DK415 | 99.9 | 28.5 | 13 | 14 |
| Furio | 108.7 | 30.8 | 11 | 6 |
| Nastia | 116.9 | 30.2 | 4 | 0 |

Further Embodiments of the Invention

This invention is also directed to methods for producing a corn plant by crossing a first parent corn plant with a second parent corn plant, wherein the first or second corn plant is the inbred corn plant from the line TDC1. Further, both first and second parent corn plants may be from the inbred line TDC1. Therefore, any methods using the inbred corn line TDC1 are part of this invention: selfing, backcrosses, hybrid breeding, and crosses to populations. Any plants produced using inbred corn line TDC1 as a parent are within the scope of this invention. Advantageously, the inbred corn line is used in crosses with other corn varieties to produce first generation ($F_1$) corn hybrid seed and plants with superior characteristics. Still further, this invention is also directed to methods for producing an inbred maize line TDC1-derived maize plant by crossing inbred maize line TDC1 with a second maize plant and growing the progeny seed, and repeating the crossing and growing steps with the inbred maize line TDC1-derived plant from 0 to 7 times.

As used herein, the term "plant" includes plant cells, plant protoplasts, plant cell of tissue culture from which corn plants can be regenerated, plant calli, plant clumps, and plant cells that are intact in plants or parts of plants, such as pollen, flowers, kernels, ears, cobs, leaves, husks, stalks, and the like.

The present invention contemplates a corn plant regenerated from a tissue culture of an inbred (e.g. TDC1) or hybrid plant of the present invention. As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, leaves, stalks, roots, root tips, anthers, and the like. In a preferred embodiment, tissue culture is embryos, protoplast, meristematic cells, pollen, leaves or anthers. Means for preparing and maintaining plant tissue culture are well known in the art. As well known in the art, tissue culture of corn can be used for the in vitro regeneration of a corn plant. Tissue culture of corn is described in European Patent Application, Publication No. 160,390, incorporated herein by reference. Corn tissue culture procedures are also described in Green and Rhodes, "Plant Regeneration in Tissue Culture of Maize", Maize for Biological Research (Plant Molecular Biology Association, Charlottesville, Va. 1982), at 367–372. A study by Duncan et al., (1985), "The production of callus capable of plant regeneration from immature embryos of numerous *Zea Mays* Genotypes", Planta, 165 :322–332, indicates that 97 percent of cultured plants produced calli capable of regenerating plants. Subsequent studies have shown that both inbreds and hybrids produced 91 percent regenerable calli that produced plant. Other studies indicate that non-traditional tissues are capable of producing somatic embryogenesis and plant regeneration. See, e.g., Songstad et al., (1988) "Effect of ACC (1-aminocyclopropane-1-carboxyclic acid), Silver Nitrate & Norbonadiene on Plant Regeneration From Maize Callus Cultures", Plant Cell Reports, 7:262–265; Rao et al., (1986)) "Somatic Embryogenesis in Glume Cultures", Maize Genetics Cooperative Newsletter, No.60, pp.64–65; and Conger et al., (1987) "Somatic Embryogenesis From Cultured Leaf Segments of *Zea Mays*", Plant Cell Reports, 6:345–347, the disclosures of which are incorporated herein by reference. Regenerable cultures may be initiated from immature embryos as described in PCT publication WO 95/06128, the disclosure of which is incorporated herein by reference.

Thus, another aspect of this invention is to provide for cells which upon growth and differentiation produce the inbred line TDC1.

The present invention encompasses methods for producing a corn plant containing in its genetic material one or more transgenes and the transgenic corn plant produced by that method.

The molecular techniques allow genetic engineering of the genome of plants by adding or modifying foreign or endogenous genes (referred to here as transgenes) in such a manner that the traits of the plant can be modified in a specific way. Plant transformation involves the construction of an expression vector comprising one or more gene under control or operatively linked to a regulatory element (e.g. a promoter). Such vector can be used to provide transformed corn plants, using transformation methods as described hereafter to incorporate the gene or the genes into the genetic material of the corn plant.

To facilitate the identification of transformed plant cells, the vector of this invention may include plant selectable markers. Selectable markers and uses are well known in the art and include enzymes which provide for resistance to antibiotics such as gentamycin (Hayford et al., Plant Physiol. 86: 1216 (1988)), hygromycin (Vanden Elzen et al., Plant Mol. Biol., 5: 299 (1985)), kanamycin (Fraley et al., Proc. Natl. Acad. Sci. U.S.A., 80: 4803 (1983)), and the like. Similarly, enzymes providing for production of a compound identifiable by colour change such as GUS, (beta.glucuronidase Jefferson, R. A., Plant Mol. Biol. Rep. 5: 387 (1987)), are useful.

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. "Tissue-specific" promoters initiate transcription only in certain tissues, such as a pollen-specific promoter from Zm13 (Guerrero et al., Mol. Gen. Genet.224: 161–168 (1993). "Inducible" promoter is under environmental control, such as the inducible promoter from a steroid hormone gene, the transcriptional activity of which is induced by a glucocorticosteroid hormone (Schena et al., Proc. Natl. Acad. Sci. U.S.A. 88: 0421 (1991)). Tissue-specific and inducible promoters are "non-constitutive" promoters. A "constitutive" promoter is a promoter which is active under most environmental conditions such as the 35S promoter from CaMV (Odell et al., Nature 313: 810–812 (1985) or the promoters from such genes as rice actin (McElroy et al., Plant Cell 2: 163–171 (1990)).

These regulatory sequences will allow the expression of the transgenes in the transformed cells, in the transformed plants. The transgenes may code for proteins including plant selectable markers but also proteins adding a value trait to the crop such as agronomic, nutritional or therapeutic value or proteins conferring resistance to diseases and/or pathogens (e.g. bacterial, fungal, insect or herbicide resistance).

Several techniques, depending on the type of plant or plant cell to be transformed, are available for the introduction of the expression construct containing a DNA sequence encoding an protein of interest into the target plants. See, for example, Miki et al., "Procedures for Introducing Foreign DNA into Plants" in Methods in Plant Molecular Biology and Biotechnology, Glick, B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, Inc., Boca Raton, 1993) pages 89–119.

Suitable methods of transforming plant or plant cells, hereby incorporated by reference, include microinjection, electroporation or Agrobacterium mediated transformation; Ti and Ri plasmids of *Agrobacterium tumefaciens* and *Agrobacterium rhizogenes,* (both plant pathogenic soil bacteria), respectively, carry genes responsible for genetic transformation of the plant. See Gruber et al., supra, Miki et al., supra.

Another applicable method of plant transformation is microprojectile-mediated transformation wherein DNA is carried on the surface of microprojectiles and accelerated to penetrate plant cell walls and membranes (Sanford, J. C., Physiol Plant 79: 206 (1990), Klein et al., Biotechnology 6: 559–563 (1988)). In maize, several target tissues can be bombarded with DNA-coated microprojectiles in order to produce transgenic plants, including, for example, callus (Type I or Type II), immature embryos, and meristematic tissue.

Following transformation of maize target tissues, expression of the above-described selectable marker genes allows for preferential selection of transformed cells, tissues and/or plants, using regeneration and selection methods now well known in the art.

The transgenic inbred lines produced by the forgoing methods could then be crossed, with another (non-transformed or transformed) inbred line, in order to produce a transgenic hybrid maize plant.

When the term inbred corn plant is used in the context of the present invention, this also includes any single gene conversions of that inbred. The term single gene converted plant as used herein refers to those corn plants which are developed by a plant breeding technique called backcrossing wherein essentially all of the desired morphological and physiological characteristics of an inbred are recovered in addition to the single gene transferred into the inbred via the backcrossing technique. Backcrossing methods can be used with the present invention to improve or introduce a characteristic into the inbred. The term backcrossing as used herein refers to the repeated crossing of a hybrid progeny back to one of the parental corn plants for that inbred. The parental corn plant which contributes the gene for the desired characteristic is termed the nonrecurrent or donor parent. This terminology refers to the fact that the nonrecurrent parent is used one time in the backcross protocol and therefore does not recur. The donor parent may, or may not be transgenic. The parental corn plant to which the gene or genes from the nonrecurrent parent are transferred is known as the recurrent parent as it is used for several rounds in the backcrossing protocol (Poehlman & Sleper, 1994,; Fehr, 1987). In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a corn plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original inbred. To accomplish this, a single gene of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new inbred but that can be improved by backcrossing techniques. Single gene traits may or may not be transgenic, examples of these traits include but are not limited to, male sterility, corn endosperm, herbicide resistance, resistance for bacterial, fungal, or viral disease, insect resistance, male fertility, enhanced nutritional quality, industrial usage, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

Industrial Applicability

The seed of inbred maize line TDC1, the plant produced from the inbred seed, the hybrid maize plant produced from the crossing of the inbred, hybrid seed, and various parts of the hybrid maize plant and transgenic versions of the foregoing, can be utilized for human food or livestock feed. They also may be used as a raw material in industry. The food uses of maize, in addition to human consumption of maize kernels, include both products of dry-milling (e.g., meal, flour) and wet-milling industries (e.g., dextrose, starch).

As livestock feed, maize is primarily used for beef cattle, dairy cattle, hogs, and poultry.

Starch Industry now uses maize and maize derived products in various productions such as papers, chemistry, and pharmacology. Plant parts other than the grain of maize are also used in industry, e.g. cobs are used for fuel and to make charcoal.

Deposit Information

A deposit of the AgReliant Genetics proprietary inbred corn line TDC1 disclosed above and recited in the appended claims has been made with the American Type Culture Collection (ATCC), 10801 University Boulevard, Manassas, Va. 20110. The date of deposit was Jun. 14, 2002. The deposit of 2,500 seeds were taken from the same deposit maintained by AgReliant Genetics since prior to the filing date of this application. All restrictions upon the deposit have been removed, and the deposit is intended to meet all of the requirements of 37 C.F.R. §1.801–1.809. The ATCC accession number is PTA-4559. The deposit will be maintained in the depository for a period of 30 years, or 5 years after the last request, or for the effective life of the patent, whichever is longer, and will be replaced as necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. An inbred corn seed designated TDC1, wherein a sample of said seed as been deposited under ATCC Accession number PTA-4459.

2. A corn plant or parts thereof, produced by growing the seed of claim 1.

3. Pollen of the plant of claim 2.

4. An ovule or ovules of the plant of claim 2.

5. A corn plant, or part thereof, having all the physiological and orphological characteristics of the corn plant of claim 2.

6. The corn plant of claim 2, wherein said plant further comprises a genetic factor conferring male sterility.

7. A tissue culture of regenerable cells of a corn plant of claim 2.

8. The tissue culture of claim 7 selected from the group consisting of protoplast and calli, wherein the regenerable cells are derived from meristematic cells, leaves, pollen, embryo, roots, root tip, anthers, silks, flowers, kernels, ears, cobs, husks, or stalks.

9. A corn plant regenerated from the tissue culture of claim 7, capable of expressing all the morphological and physiological characteristics of inbred corn plant TDC1.

10. A corn plant with all the physiological and morphological characteristics of the corn inbred TDC1, wherein said corn plant is produced by a tissue culture process using the corn plant of claim 5 as the starting material for such a process.

11. A method for producing a hybrid corn seed comprising crossing a first inbred parent corn plant with a second inbred parent corn plant and harvesting the resultant hybrid corn seed, wherein said first or second parent corn plant is the corn plant of claim 2.

12. A hybrid corn seed produced by the method of claim 11.

13. A hybrid corn plant, or parts thereof, produced by growing said hybrid corn seed of claim 12.

14. Corn seed produced by growing said hybrid corn plant of claim 13 and harvesting the resultant seed.

15. A method for producing a hybrid corn seed comprising crossing an inbred plant according to claim 2 with another, different corn plant.

16. A hybrid corn seed produced by the method of claim 15.

17. A hybrid corn plant, or its parts, produced by growing said hybrid corn seed of claim 16.

18. Corn seed produced from said hybrid corn plant of claim 17.

19. A method for producing a TDC1-derived corn plant, comprising:
   a) crossing inbred corn line TDC1, a sample of seed of said line having been deposited under ATCC accession number PTA-4459, with a second corn plant to yield progeny corn seed; and
   b) growing said progeny corn seed, under plant growth conditions, to yield said TDC1-derived corn plant.

20. The method of claim 19, further comprising:
   c) crossing said TDC1-derived corn plant with itself or another corn plant to yield additional TDC1-derived progeny corn seed;
   d) growing said progeny corn seed of step (c) under plant growth conditions, to yield additional TDC1-derived corn plants; and
   e) repeating the crossing and growing steps of (c) and (d) from 0 to 7 times to generate further TDC1-derived corn plants.

21. The method of claim 19, still further comprising utilizing plant tissue culture methods to derive progeny of said TDC1-derived corn plant.

22. The corn plant, or parts thereof, of claim 2, wherein the plant or parts thereof have been transformed so that its genetic material contains one or more transgenes operably linked to one or more regulatory elements.

23. A method for producing a corn plant that contains in its genetic material one or more transgenes, comprising crossing the corn plant of claim 22 with either a second plant of another corn line, or a non4ransformed corn plant of the line TDC1, so that the genetic material of the progeny that result from the cross contains the transgene(s) operably linked to a regulatory element.

24. Corn plants, or parts thereof, produced by the method of claim 23.

25. A method for developing a corn plant in a corn plant breeding program using plant breeding techniques which include employing a corn plant, or its parts, as a source of plant breeding material comprising: obtaining the corn plant, or its parts, of claim 2 as a source of said breeding material wherein said breeding techniques are selected from the group consisting of: recurrent selection, backcrossing, pedigree breeding, restriction fragment length polymorphism enhanced selection, genetic marker enhanced selection and transformation.

26. The corn plant of claim 5, further comprising a single gene conversion.

27. The corn plant of claim 26, further comprising a cytoplasmic factor conferring male sterility.

28. The single gene conversion corn plant of claim 26, where the gene is selected from the group consisting of: a transgenic gene, a dominant allele and a recessive allele.

29. The single gene conversion corn plant of claim 26, where the gene confers a characteristic selected from the group consisting of: herbicide resistance, insect resistance, resistance to bacterial, fungal, or viral disease, male sterility, corn endosperm, and improved nutritional quality.

* * * * *